United States Patent [19]
Liegeois et al.

[11] Patent Number: 5,393,752
[45] Date of Patent: Feb. 28, 1995

[54] METHYLPIPERAZINOAZEPINE COMPOUNDS, PREPARATION AND USE THEREOF

[75] Inventors: Jean-Francois F. Liegeois, Herstal; Jacques E. Delarge, Dolembreux, both of Belgium

[73] Assignee: Therabel Research S.A./N.V., Brussels, Belgium

[21] Appl. No.: 261,237

[22] Filed: Jun. 14, 1994

Related U.S. Application Data

[63] Continuation of Ser. No. 888,372, May 26, 1992, abandoned.

[51] Int. Cl.$^6$ .................. C07D 403/04; C07D 413/04; C07D 417/04; A61K 31/55
[52] U.S. Cl. .................................. 514/211; 540/548; 540/551; 540/554; 540/557; 514/220
[58] Field of Search ................ 514/211, 220; 540/548, 540/551, 554, 557

[56] References Cited

U.S. PATENT DOCUMENTS

| | | | |
|---|---|---|---|
| 3,872,122 | 3/1975 | Juby | 260/256.4 |
| 4,163,785 | 8/1979 | Hoffmann | 424/250 |
| 4,337,198 | 6/1982 | Sorg | 260/243.3 |

FOREIGN PATENT DOCUMENTS

| | | |
|---|---|---|
| 0003016 | 7/1979 | European Pat. Off. . |
| 0354781 | 2/1990 | European Pat. Off. . |
| 0413300 | 2/1991 | European Pat. Off. . |
| 2222102 | 10/1974 | France . |
| 2456104 | 12/1980 | France . |

OTHER PUBLICATIONS

Dupont et al., Chemical Abstracts, vol. 115, entry 194749n (1991).
Sbit et al., Chemical Abstracts, vol. 108, entry 141092s (1988).
Dupont et al., Chemical Abstracts, vol. 106, entry 205611d (1987).
Hoffmann et al., Chemical Abstracts, vol. 91, entry 157779n (1979).
Hoffmann et al., Chemical Abstracts, vol. 90, entry 23134u (1979).
Journal of Medicinal Chemistry, (1989), vol. 32, No. 10 (Wash., D.C., U.S.), J. K. Chakrabarti et al.: "Synthesis and Pharmacological Evaluation of CNS Activities of (1,2,3)triazolo(4,5-b)(1,5)-, imidazolo(4,5-b)(1,5)-, and pyrido(2,3-b)(1,5)(benzodiazepines. 10-Piperazinyl-4-H-1,2,3-triazolo(4,5-b)(1,5)benzodiazepines with neuroleptic activity", pp. 2375–2381.
Behavorial Pharmacology (1992), 3, 567–579, J. Bruhwyler et al, "Comparative Study of Typical Neuroleptics, Clozapine and Newly Synthesized Chlozapine-Analogues: Correlations Between Neurochhemistry and Behavior".
Acta Cryst. (1987), C43, 716–718, L. Dupont et al. "Structure du Maléate de Méthyl-l(Pyrido[2,3-f][1,5-]benzoxazépinyl-5)1H+ Pipérazinium".

(List continued on next page.)

*Primary Examiner*—John M. Ford
*Attorney, Agent, or Firm*—Sughrue, Mion, Zinn, Macpeak & Seas

[57] ABSTRACT

Methylpiperazinoazepine derivatives corresponding to formula (I):

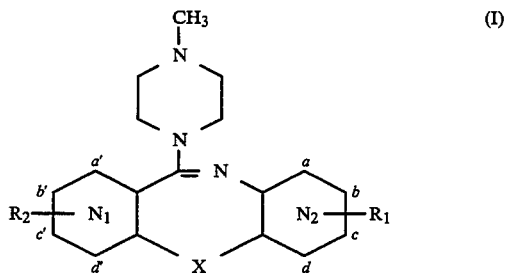

wherein the symbols X, $R_1$, $R_2$, $N_1$ and $N_2$ have different meanings and pharmaceutically acceptable salts thereof, preparation and use thereof.

17 Claims, No Drawings

OTHER PUBLICATIONS

Acta Crysta. (1988) C44, 319–321, Olszak et al, "Structure du(Méthyl-1 pipérazinyl-4)-5 Pyrido[2,3-b][1,5-]benzothiazépine".

Acta Crysta. (1991) c47, 1740–1742, Dupont et al, "Structure du(Méthyl-4 pipérazinyl-1)-10 Pyrido[4,3-b][1,4]benzothiazépine".

Acta Crystallographica, vol. C47, Part 8, pp. 1573–1776, Aug. 15, 1991, "Table of Contents".

Acta Crysta. (1991) C47, 2690–2693, Dupont et al, "Structures du 11- Forml-5-(4-methylpiperazin-1-yl)-11 H-pyrido-[2,3-b][1,5]benzodiazepine et du 6-(-4-Methylpiperazin-1-yl)-11-methyl-11 H-pyrido-[2,3-b][1,4]benzodiazepine".

METHYLPIPERAZINOAZEPINE COMPOUNDS, PREPARATION AND USE THEREOF

This is a continuation of application Ser. No. 07/888,372, filed May 26, 1992, now abandoned.

The present invention relates to new methylpiperazinoazepine derivatives and to their non-toxic salts, as well as to the preparation of these new compounds and to their therapeutical use.

The new methylpiperazinoazepines of the invention are represented by formula (I):

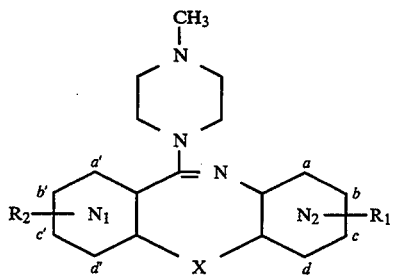

wherein:

X represents an oxygen atom, a sulfur atom, a selenium atom or an NH- or $NR_3$-group wherein $R_3$ represents a

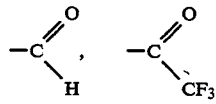

group or branched alkyl group of 1 to 4 carbon atoms;

$R_1$ represents a hydrogen atom, a halogen atom or a straight or branched alkyl group of 1 to 4 carbon atoms;

$R_2$ represents a hydrogen atom, a halogen atom or a straight or branched alkyl group of 1 to 4 carbon atoms; and $N_1$ represents a benzene ring and $N_2$, a pyridine ring or vice versa, with the provision that, when $R_1$ and $R_2$ represent hydrogen and X represents sulfur, oxygen or an NH-group, $N_1$ is pyridine and $N_2$ benzene, and the pyridine nitrogen is excluded from position d'. Both $N_1$ and $N_2$ can further be benzene when X represents a selenium atom.

A certain number of methylpiperazinoazepine derivatives of this type have already been reported in literature. Reference will be made to the articles of Dupont et al., Acta cryst., C43, 716–718, 1987 for the oxygen derivative; Hoffmann et al., U.S. Pat. No. 4,163,785, 1979 for the sulfur compound; and Chakrabarti et al., Journal of Medicinal Chemistry, vol. 32, No. 10, 2375–2381, 1989 for the nitrogen derivative. However, in contrast to the derivatives of the present invention, no methylpiperazinoazepine of this type described up to now presents an interesting pharmacological activity.

As it has already been mentioned hereinabove, the methylpiperazinoazepine derivatives of the present invention are represented by the general formula (I). The straight or branched alkyl group of 1 to 4 carbon atoms in the aforesaid general formula can be, for example, methyl, ethyl, n-propyl, isopropyl, n-butyl, isobutyl and tert-butyl groups. As to the term halogen, this includes chlorine, fluorine, iodine and bromine.

Preferred classes of compounds according to formula (I) are more particularly the class wherein $R_1$ represents a hydrogen atom, a chlorine atom, a fluorine atom or a methyl group and the class wherein $R_2$ represents a hydrogen atom or a chlorine atom. A particularly preferred class of these compounds is one wherein $R_1$ represents hydrogen, chlorine, fluorine or methyl and, simultaneously, wherein $R_2$ represents hydrogen or chlorine.

The derivatives according to formula (I) which may be in the form of non-toxic salts, are in particular salts of inorganic acids, such as hydrochlorides, hydrobromides, phosphates, sulfates or salts of organic acids such as acetates, citrates, maleates, fumarates and methanesulfonates.

Examples of derivatives according to the invention are:

11-(4-methylpiperazin-1-yl)-5H-pyrido(4,3-b)benzo-1,5-diazepine;

6-(4-methylpiperazin-1-yl)pyrido(2,3-b)benzo-1,4-thiazepine;

8-chloro-6-(4-methylpiperazin-1-yl)pyrido(2,3-b)benzo-1,4-thiazepine fumarate;

5-(4-methylpiperazin-1-yl)pyrido(2,3-b)benzo-1,5-oxazepine maleate;

8-chloro-5-(4-methylpiperazin-1-yl)pyrido(2,3-b)benzo-1,5-oxazepine fumarate;

5-(4-methylpiperazin-1-yl)-8-methylpyrido(2,3-b)benzo-1,5-oxazepine fumarate;

6-(4-methylpiperazin-1-yl)pyrido(2,3-b)benzo-1,4-oxazepine fumarate;

8-chloro-6-(4-methylpiperazin-1-yl)pyrido(2,3-b)benzo-1,4-oxazepine fumarate;

6-(4-methylpiperazin-1-yl)-11H-pyrido(2,3-b)benzo-1,4-diazepine;

8-chloro-6-(4-methylpiperazin-1-yl)-11H-pyrido(2,3-b)benzo-1,4-diazepine;

6-(4-methylpiperazin-1-yl)-8-methyl-11H-pyrido(2,3-b)benzo-1,4-diazepine;

9-chloro-6-(4-methylpiperazin-1-yl)-11H-pyrido(2,3-b)benzo-1,4-diazepine;

8-fluoro-6-(4-methylpiperazin-1-yl)-11H-pyrido(2,3-b)benzo-1,4-diazepine;

5-formyl-11-(4-methylpiperazin-1-yl)-5H-pyrido(4,3-b)benzo-1,5-diazepine;

11-formyl-5-(4-methylpiperazin-1-yl)-11H-pyrido(2,3-b)benzo-1,5-diazepine;

11-trifluoromethylcarbonyl-5-(4-methylpiperazin-1-yl)-11H-pyrido(2,3-b)benzo-1,5-diazepine;

11-formyl-6-(4-methylpiperazin-1-yl)-11H-pyrido(2,3-b)benzo-1,4-diazepine;

10-(4-methylpiperazin-1-yl)pyrido(4,3-b)benzo-1,4-thiazepine;

5-(4-methylpiperazin-1-yl)dibenzo(b,f)1,4-selenazepine;

6(4-methylpiperazin-1-yl)dipyrido(2,3-b:3',2'-f)1,4-thiazepine;

6-(4-methylpiperazin-1-yl)-11-methyl-11H-pyrido(2,3-b)benzo-1,4-diazepine.

The new compounds according to the invention can be prepared according to the general process which is the subject of the present invention starting from known or easily synthesized azepinones corresponding to formula (II):

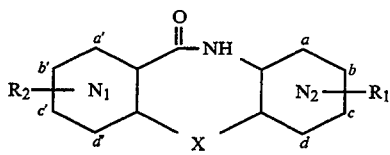

(II)

wherein X, $R_1$ and $R_2$ are such as defined hereinabove and wherein both $N_1$ and $N_2$ represent a benzene or pyridine ring.

In this respect, a certain number of azepinones which are already described in the literature are given hereinafter:

5,11-dihydro-6H-pyrido(2,3-b)benzo-1,4-diazepine-6-one;
6,11-dihydro-5H-pyrido(2,3-b)benzo-1,5-diazepine-5-one;
5,10-dihydro-11H-pyrido(4,3-b)benzo-1,5-diazepine-11-one;
5,11-dihydro-11-methyl-6H-pyrido(2,3-b)benzo-1,4-diazepine-6-one;
5H,6H-pyrido(2,3-b)benzo-1,5-oxazepine-5-one;
5H,6H-pyrido(2,3-b)benzo-1,4-oxazepine-6-one;
5,11-dihydro-8-methyl-6H-pyrido(2,3-b)benzo-1,4-diazepine-6-one;
9-chloro-5,11-dihydro-6H-pyrido(2,3-b)benzo-1,4-diazepine-6-one;
10H,11H-dibenzo(b,f)1,4-selenazepine-11-one.

The last mentioned azepinone, i.e. 10H,11H-dibenzo(b,f)1,4-selenazepine-11-one could also have been prepared starting from dibromo-2,2'-benzanilide. To do this, 150 ml dry dimethylformamide, 0.015 moles selenium, 0.050 moles sodium are, for example, introduced into a balloon-flask. The mixture is heated to 100° C. while agitating for four hours. When the mixture is dissolved, 0.025 moles dibromo-2,2'-benzanilide are added and the agitation is continued for 20 hours at 100° to 110° C. The solution is poured onto a mixture of hydrochloric acid and ice. The precipitate is filtered. The obtained product is treated with boiling alcohol and filtered. The derivative is recrystallized from a mixture of dimethylformamide and water. The melting point is 275° C.

The synthesis of a certain number of original azepinones which have not been described in the literature can be found hereinafter.

Preparation 1

8-chloro-5H,6H-pyrido(2,3-b)benzo-1,5-oxazepine-5-one (formula II: X=O, $R_1$=Cl in position b, $R_2$=H, $N_1$=pyridine with N in position d', $N_2$=benzene)

A solution of 2-chloro-pyridine-3-carboxylic acid chloride (0.1 mole) is poured little by little onto a solution of 2-amino-4-chloro-phenol (0.2 moles) in tetrahydrofuran (150 ml). It is kept under reflux agitation for one hour. It is diluted with one liter water. The formed precipitate is collected, washed and dried. The raw product is used for the following step. The oxazepine is prepared by treating the amide by the theoretical quantity of sodium ethylate in absolute alcohol. The sodium salt is isolated by evaporating the solvent. The desired cyclization is obtained by heating with reflux for 3 to 4 hours in dimethylformamide. The mixture is concentrated by vacuum distillation of the DMF and is crystallized at 0° C. The isolated product is washed with cold methanol and recrystallized from a mixture of DMF/methanol. The melting point is 300° C.

Preparation 2

5H,6H-8-methyl-pyrido(2,3-b)benzo-1,5-oxazepine-5-one (formula II: X=O, $R_1$=CH$_3$ in position b, $R_2$=H, $N_1$=pyridine with N in d', $N_2$=benzene)

This substance has been prepared according to the process of preparation 1, wherein use was made of 2-chloro-pyridine-3-carboxylic acid and of 2-amino-4-methylphenol as starting materials. Melting point: 203° C.

Preparation 3

8-chloro-5H,6H-pyrido(2,3-b)benzo-1,4-oxazepine-6-one (formula II: X=O, $R_1$=H, $R_2$=Cl in position b', $N_1$=benzene, $N_2$=pyridine with N in position d).

The phenolic ester of 5-chloro-salicylic acid is prepared by refluxing 0.1 mole phenol and 0.1 mole 5-chloro-salicylic acid in the presence of an excess of OPCl$_3$ for 2 hours. The reagent is removed under vacuum. The obtained pasty, mass is progressively taken up with water. The formed precipitate is filtered and washed with water. The melting point is 89° C.

The desired compound is obtained by heating to melting 0.05 moles of the hereabove prepared ester with 0.1 mole of 3-amino-2-chloro-pyridine until the end of reaction. The mass is taken up with 30 ml ethanol and triturated until a filterable precipitate is obtained. After isolation, the product is washed with ethanol and recrystallized from dioxane or from a mixture of DMF/methanol. The melting point is 280° C.

Preparation 4

5H,6H-pyrido(2,3-b)benzo-1,4-thiazepine-6-one (formula II: X=S, $R_1$=$R_2$=H, $N_1$=benzene, $N_2$=pyridine with N in position d)

Process 1:

a) Preparation of 2-(phenylthio)pyridine-3-carboxylic acid. 0.2 moles thiophenol and 0.2 moles 50% NaH are dispersed into 50 cc propylene glycol. To this mixture is added 0.1 mole 2-chloropyridine-3-carboxylic acid and it is brought to a boil. After reaction, the solvent is evaporated. The residue is taken up with water and it is brought to pH 7. The excess of thiophenol is extracted with chloroform. The aqueous phase is purified with active carbon and acidified. The product precipitates in the form of a white powder. The melting point is 164° C.

b) The previous compound is transformed into azide by reaction of the hereabove prepared acid chloride. The acid chloride is poured into an excess of a cooled sodium azide solution. Once the addition is terminated, it is kept under agitation during ¼ hour and diluted with water. The product is isolated and used as such after drying for the following reaction. The cyclization of the compound is realized by the following technique. 1 g raw azide is added little by little to a solution of AlCl$_3$ in orthodichlorobenzene to 120° C. and under agitation. The temperature is maintained during ½ hour. The mixture is then taken up with chloroform and extracted with N/10 hydrochloric acid. The acid phase is reextracted several times with ClCH$_3$. The chloroformic phases are brought together, dried and concentrated under vacuum. The residue is taken up with acetone and left for 2 hours in the refrigerator. The precipitate is collected onto a filter. The melting point is 206°-208° C.

Process 2:

0.01 mole 3-amino-2-chloro-pyridine is heated to melting until the end of the reaction with 0.01 mole 2-thiosalicylic acid. After cooling down, the residue is taken up with 30 ml ethanol. It is boiled for some minutes and then allowed to cool down. The precipitate is collected onto a filter, washed with ethanol and dried. The melting point is 205° to 208° C.

Preparation 5

5H,6H-pyrido(4,3-b)benzo-1,4-thiazepine-6-one (formula II:: X=S, $R_1=R_2=H$, $N_1$=benzene, $N_2$=pyridine with N in position b)

0.01 mole thiosalicylic acid and 0.01 mole 3-aminino-4-chloropyridine are heated with reflux for a few hours in the presence of orthodichlorobenzene. When the reaction is terminated, the solvent is eliminated. The residue is taken up with a little water and brought to a pH of 5-6. The compound is extracted into chloroform. The CHCl$_3$ extracts are evaporated. The residue is taken up with an aqueous solution of bicarbonate and agitated for ½ hour. The suspended compound is collected onto a filter and washed with water. The melting point is 244° C.

Preparation 6

8-chloro-5H,6H-pyrido(2,3-b)benzo-1,4-thiazepine-6-one (formula II: X=S, $R_1$=H, $R_2$=Cl in position b', $N_1$=benzene, $N_2$=pyridine with N in position d)

The compound is obtained according to the method described in Preparation 4, Process 1. The melting point is 314° C.

Preparation 7

5H,6H-dipyrido(2,3-b:3',2'-f)1,4-thiazepine-5-one (formula II: X=S, $R_1=R_2=H$, $N_1=N_2$=pyridine with N in position d and d')

Starting from 1.575 g 2-chloropyridine-3-carboxylic acid, the acid chloride is prepared by reaction with thionyl chloride. After evaporation of the excess of reactant, the residue is taken up with 20 ml dioxane and poured little by little on a solution of 3.12 g 3-amino-2-mercaptopyridine in 50 ml dioxane while agitating thoroughly. It is kept shaking for ¼ hour and then diluted with five times its volume of water. Everything goes in solution and the medium is slightly acid, the precipitate being optionally eliminated. The pH is adjusted to 7 with bicarbonate and the solution is allowed to crystallize. The obtained product is dried in a ventilated drying-oven and is recrystallized, if necessary, in toluene. The melting point is 183° C.

0.01 mole of the amide derivative is added to a suspension of 0.012 moles tert-butylate of Na in 50 ml DMF. It is heated with reflux for 10 to 20 hours, the DMF is evaporated under vacuum and the residue is taken up with water (50 ml). The precipitate is filtered, washed with water and dried. Once dry, it is taken up with ether and triturated. After filtration and drying, the product can, if necessary, be recrystallized in DMF. The melting point is 305° C.

Preparation 8

8-chloro-5H,6H-pyrido(2,3-b)benzo-1,4-thiazepine-6-one (formula II: X=NH, $R_1$=Cl in position b', $R_2$=H $N_1$=benzene, $N_2$=pyridine with N in position d)

1) 0.01 mole of 5-chloro-2-nitrobenzoic acid is refluxed with 20 ml SOCl$_2$ and a few drops of DMF during one hour. The excess of SOCl$_2$ is eliminated, the residue is taken up with 20 ml dioxane. This solution is added little by little to a solution of 0.015 moles 3-amino-2-chloropyridine in 20 ml dioxane. After one hour under agitation, the mixture is diluted with five times its volume of water. The precipitate is filtered and washed with cold water. If necessary, the product is recrystallized from isopropanol. The melting point is 190° C.

2) 0.01 mole —NO$_2$ derivative is dissolved in 25 ml concentrated HCl. To this solution, 11 g SnCl$_2$.2H$_2$O dissolved in 20 ml concentrated HCl, is added little by little. The resulting solution is then placed for one hour in a water bath. After cooling down, the precipitate is filtered, taken up with 10% NaOH and extracted in chloroform. The chloroformic phase is dried and concentrated to a small volume in the presence of petrolein 100-140. The crystallized product is then filtered and washed with petrolein 40-60. The melting point is 173° C.

3) 0.01 mole of the amino derivative prepared according to 2) is dissolved in 18 ml diethylene glycol monomethyl ether. 0.2 ml of 5% HCl are added. The mixture is brought to 130° C. under agitation. After 2 to 3 hours heating, a suspension is obtained. As soon as the reaction is terminated, the mixture is cooled down and filtered. The isolated product is washed with cold methanol and recrystallized, if necessary, in dioxane. The melting point is 296° C.

Preparation 9

5,11-dihydro-8-fluoro-6H-pyrido(2,3-b)benzo-1,4-diazepine-6-one (formula II: X=NH, $R_1$=F in position d', $R_2$=H, $N_1$=benzene, $N_2$=pyridine with N in position d)

This compound is prepared according to the Method of Preparation 8, but starting from 5-fluoro-2-nitrobenzoic acid and 3-amino-2-chloropyridine. The meling point is 270° C.

The general process for obtaining the methyl-piperazinoazepines of formula (I) of the invention starting from the azepinones of formula (II) can be carried out according to three embodiments, the schemes of which are given and commented hereinafter.

Scheme A:

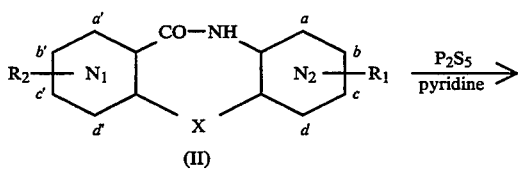

(II)

-continued
Scheme A:

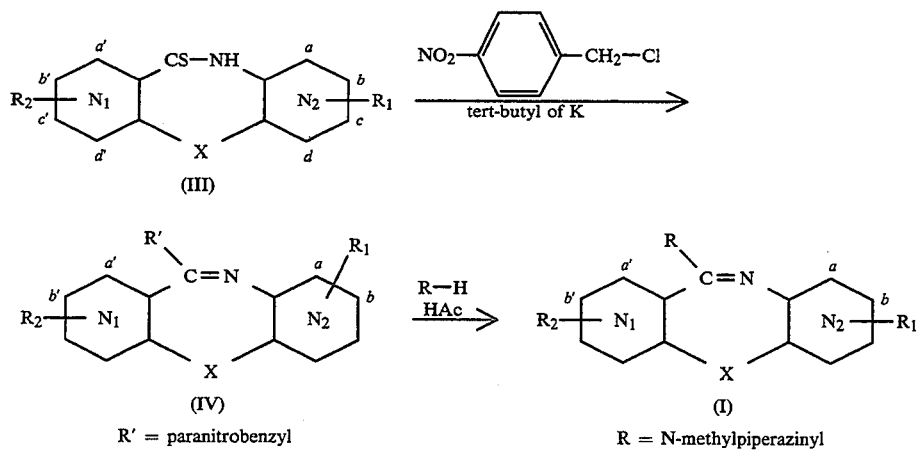

R' = paranitrobenzyl

R = N-methylpiperazinyl

Starting from the azepinone (II), the corresponding thione (III) is synthesized by action of $P_2S_5$ in pyridine. The raw product is isolated, used as such and added with tert-butylate of potassium and paranitrobenzyl chloride to prepare thioether (IV). The compound of formula (I) is obtained after reaction of the thioether in the presence of N-methylpiperazine and glacial acetic acid. (See in this respect Hunzicker et al., Helv. Chim. Acta, 50, 1588, 1967).

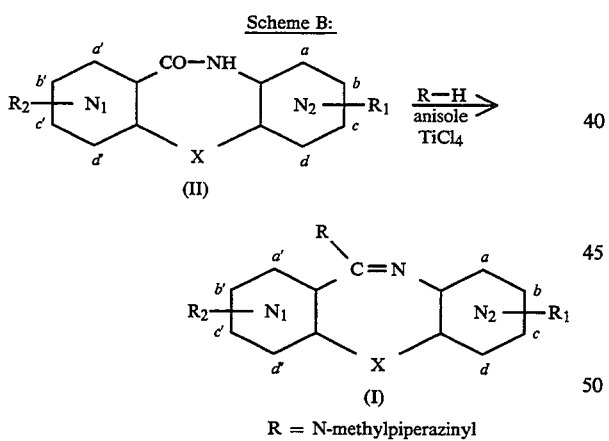

R = N-methylpiperazinyl

The azepinone (II) is admixed with the N-methylpiperazine in the presence of a solution of $TiCl_4$ in anisole. After agitation and heating, compound (I) of the invention is obtained. (See in this respect Chakrabarti J. K. et al., J. Med. Chem. 23, 878, 1980 and Press J. et al., J. Med. Chem. 22, 725, 1979)

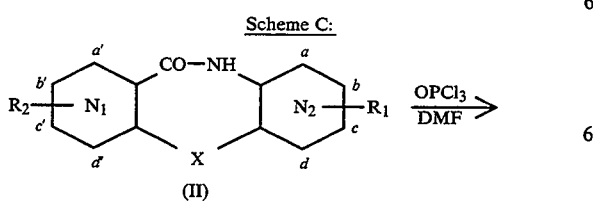

-continued
Scheme C:

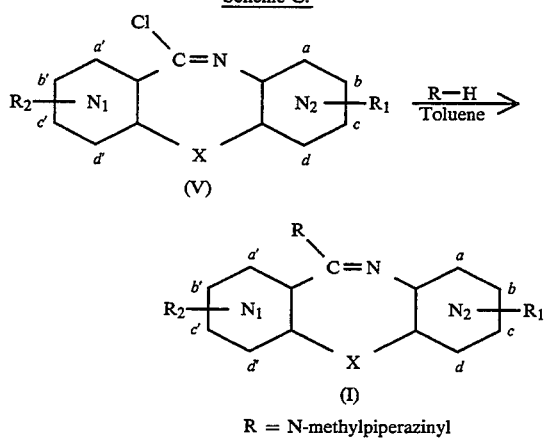

R = N-methylpiperazinyl

This scheme starts from the azepinone (II) which is treated with $OPCl_3$ and with DMF to obtain the corresponding iminochloride (V) which is reacted without further isolation and condensation with N-methylpiperazine in toluene to obtain compound (I). (See in this respect, Hunzicker F. et al., Helv. Chim. Acta 49 (5), 1933, 1966).

Of course, it is also possible to synthesize the compounds of the invention without using azepinones (II) as starting materials or intermediates, as will be shown hereinafter with reference to the synthesis of the methylpiperazinoazepine of Example 21, starting from the reaction product of an orthohalogeno nitropyridine of formula (V):

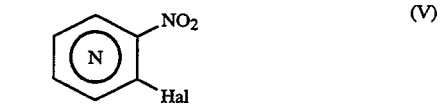

wherein Hal represents a halogen atom, such as Cl, F, I, or Br, and a benzenecarboxylic acid of formula (VI):

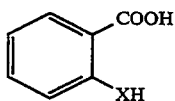

wherein X is such as defined previously.

The salts of the methylpiperazinoazepines of formula (I) can be formed with methods which are well known in practice. In a general way, these salts can be formed by reaction of the methylpiperazinoazepine with an equimolecular amount of an acid in an adequate solvent, such as for example an alcohol, possibly followed by a precipitation of the salt by adding another solvent such as ether, which is miscible with the first and wherein the salt is insoluble, or further by a neutralization of an etherial solution of the acid or the base by the base or the acid. The used acids are either organic acids or inorganic acids. As inorganic acid, use is preferably made of hydrochloric acid, hydrobromic acid, sulfuric acid, phosphoric acid, perchloric acid, etc. The organic acids are either carboxylic acids or sulfonic acids, such as acetic, citric, maleic, fumaric, propionic, glycolic, lactic, ascorbic, pamoic, succinic, tartaric, phenylacetic, benzoic, p-amino-benzoic, anthranilic, p-hydroxybenzoic, salicylic, methanesulfonic, ethanedisulfonic, glucuronic acids, etc.

Detailed examples of preparations of some methylpiperazinoazepine derivatives according to the invention are given hereinafter.

EXAMPLE 1

11-(4-methylpiperazin-1-yl)-5H-pyrido(4,3-b)benzo-1,5-diazepine (formula I: X=NH, $R_1=R_2=H$, $N_1$=pyridine with N in position b', $N_2$=benzene)

Process A:

1) 0.01 mole 5,10-dihydro-11H-pyrido(4,3-b)benzo-1,5-diazepine-11-one is treated with an excess of $P_2S_5$ in reflux heated pyridine. After a few hours of heating, the excess of solvent and reactant is eliminated. The residue is taken up carefully with ice. The formed precipitate is isolated and used as such for the following step.

2) 5.2 g of the thiolactam are added to a suspension of tert-butylate of potassium in 80 ml dioxane (prepared in the following way: 1.64 g potassium are dissolved in 40 ml tert-butanol; after the gas liberation has ceased, the solvent is eliminated and the residue is taken up with 80 ml dioxane). The mixture is refluxed for one hour. Then, 4.1 g paranitrobenzyl chloride are added. The resulting solution is refluxed for four hours. The solvent is eliminated. The residue is taken up with chloroform and washed with an alkaline lye. The chloroformic phase is dried and evaporated to dryness. The residue is recrystallized from a mixture of petrolein/acetone. The melting point is 127° C.

3) 4.3 g of the thioether prepared in 2) are heated with reflux during 24 hours in the presence of N-methylpiperazine (10 ml) and of 0.1 ml glacial acetic acid. After evaporation to dryness, the residue is taken up with diluted acetic acid. The possible precipitate is filtered. The filtrate is decolored by an active carbon treatment. The base is precipitated by adding concentrated ammonia, filtered, washed with water and dried. The product can be recrystallized from a dichloromethane/hexane mixture. The melting point is 216° C.

Process B:

0.01 mole 5,10-dihydro-11H-pyrido(4,3-b)benzo-1,5-diazepine-11-one is mixed with 10 ml N-methylpiperazine. While agitating, a solution of 1.2 ml $TiCl_4$ in 5 ml anizole is added carefully to the diazepinone suspension. The reaction is maintained under agitation for 2-3 hours at 120° C. The mixture is cooled down and taken up with ice water. The pH of the solution has to be alkaline. The product is then extracted with dichloromethane. After evaporation of the solvent, the residue is purified on a kieselgel column (eluent phase: acetone/petrolein 40-60: 9/1). After eliminating the eluent, the product is recrystallized from hexane. The melting point is 216° C.

EXAMPLE 2

6-(4-methylpiperazin-1-yl)pyrido(2,3-b)benzo-1,4-thiazepine (formula I: X=S, $R_1=R_2=H$, $N_1$=benzene, $N_2$=pyridine with N in position d)

3 g 5H, 6H-pyrido(2,3-b)benzo-1,4-thiazepine-6-one are refluxed with an excess of phosphorous oxychloride and 5 drops of N,N-dimethylaniline for 20 hours. The solution is taken up with anhydrous toluene and evaporated to dryness. The residue is taken up with 5 ml anhydrous toluene and an excess of N-methylpiperazine is added. This mixture is then refluxed for 2-4 hours. Once the reaction is terminated, the solvent is eliminated. The colored mass is taken up with chloroform and washed two times with water. The chloroformic phase is decolored with carbon and dried. After concentration into a small volume, the mixture is passed through a silica column (Woelm act III). The eluent phase is acetone. Once separated, the different phases containing the above mentioned product are evaporated to dryness. The residue is recrystallized in petrolein 100/140. The melting point is 134° C.

EXAMPLE 3

8-chloro-6-(4-methylpiperazin-1-yl)pyrido(2,3-b)benzo-1,4-thiazepine fumarate (formula I: X=S, $R_1$=H, $R_2$=Cl in b', $N_1$=benzene, $N_2$=pyridine with N in position d)

Starting from 5H,6H-pyrido(2,3-b)benzo-1,4-oxazepine-6-one, the above mentioned methylpiperazinoazepine base is prepared according to the method of Example 2. After evaporation of the chloroformic fractions, the base is dissolved into a minimum of boiling alcohol. The equimolecular quantity of fumaric acid which has been dissolved previously in hot alcohol, is added. The solution is cooled down. If the product is not crystallized by allowing it to stand, ether is added until crystallization is obtained. After allowing to stand, the obtained white precipitate is isolated and washed with ether. The melting point is 198° C.

EXAMPLE 4

5-(4-methylpiperazin-1-yl)pyrido(2,3-b)benzo-1,5-oxazepine maleate (formula I: X=O, $R_1=R_2=H$, $N_1$=pyridine with N in position d', $N_2$=benzene)

Product prepared from 5H,6H-pyrido(2,3-b)benzo-1,5-oxazepine-5-one with the process of Example 2. The chloroformic fractions are then evaporated to dryness. The residue is taken up with methylethylketone. An equimolecular amount of maleic acid dissolved in methylethylketone is added and then anhydrous ether. The product crystallizes. It is isolated and washed with ether. The melting point is 206° C.

EXAMPLE 5

8-chloro-5-(4-methylpiperazin-1-yl)pyrido(2,3-b)benzo-5-oxazepine fumarate (formula I: X=O, $R_1$=Cl in position b, $R_1$=H, $N_1$=pyridine with N in position d', $N_2$=benzene)

Starting from the oxazepine described in Preparation 1 and with use of the process of Example 2, the compound is isolated as a fumarate in the same way is in Example 3. The melting point is 260° C.

EXAMPLE 6

5-(4-methylpiperazin-1-yl)-8-methylpyrido(2,3-b)benzo-1,5-oxazepine fumarate (formula I: X=O, $R_1$=$CH_3$ in b, $R_2$=H, $N_1$=pyridine with N in position d', $N_2$=benzene)

Starting from the axozepine described in Preparation 2 and with use of the process of Example 2, the compound is isolated as a fumarate in the same way as in Example 3. The melting point is 235° C.

EXAMPLE 7

6-(4-methylpiperazin-1-yl)pyrido(2,3-b)benzo-1,4-oxazepine fumarate (formula I: X=O, $R_1$=$R_2$=H, $N_1$=benzene, $N_2$=pyridine with N in position d)

Starting from 5H,6H-pyrido(2,3-b)benzo-1,4-oxazepine-6-one and with use of the process of Example 2, the compound is isolated as a fumarate. The melting point is 183° C.

EXAMPLE 8

8-chloro-6-(4-methylpiperazin-1-yl)pyrido(2,3-b)benzo-1,4-oxazepine fumarate (formula I: X=O, $R_1$=H, $R_2$=Cl in position b', $N_1$=benzene $N_2$=pyridine with N in position d)

Starting from 8-chloro-5H,6H-pyrido(2,3-b)benzo-1,4-oxazepine-6-one of Preparation 3, the compound is prepared according to the process described in Example 2. The compound is isolated as a fumarate in the same way as in Example 3. The melting point is 250° C.

EXAMPLE 9

6-(4-methylpiperazin-1-yl)-11H-pyrido(2,3-b)benzo-1,4-diazepine (formula I: X=NH, $R_1$=$R_2$=H, $N_1$=benzene, $N_2$=pyridine with N in position d)

Starting from 5,11-dihydro-6H-pyrido(2,3-b)benzo-1,4-diazepine-6-one, the condensation according to the process B of Example 1 is performed. The melting point is 141° C.

EXAMPLE 10

8-chloro-6-(4-methylpiperazin-1-yl)-11H-pyrido(2,3-b)benzo-1,4-diazepine (formula I: X=NH $R_1$=Cl in b', $R_2$=H, $N_1$=benzene, $N_2$=pyridine with N in d)

Starting from the thiazepinone of Preparation 8, the above mentioned product is obtained according to the operation mode described in Example 1, Process B. The melting point is 180° C.

EXAMPLE 11

6-(4-methylpiperazin-1-yl)-8-methyl-11H-pyrido(2,3-b)benzo-1,4-diazepine (formula I: X=NH, $R_1$=$CH_3$ in b', $R_2$=H, $N_1$=benzene, $N_2$=pyridine with N in d)

Starting from 5,11-dihydro-8-methyl-6-H-pyrido(2,3-b)benzo-1,4-thiazepine-6-one, the above mentioned compound is prepared according to the operation mode of Example 1, process B. The melting point is 157° C.

EXAMPLE 12

9-chloro-6-(4-methylpiperazin-1-yl)-11H-pyrido(2,3-b)benzo-1,4-diazepine (formula I: X=NH, $R_1$=Cl in c', $R_2$=H, $N_1$=benzene, $N_2$=pyridine with N in d)

Starting from 9-chloro-5,11-dihydro-6H-pyrido(2,3-b)benzo-1,4-diazepine-6-one, the above mentioned product is prepared according to the operation mode of Example 1, process B. The melting point is 186° C.

EXAMPLE 13

8-fluoro-6-(4-methylpiperazin-1-yl)-11H-pyrido(2,3-b)benzo-1,4-diazepine (formula I: X=NH, $R_1$=F in b', $R_2$=H $N_1$=benzene, $N_2$=pyridine with N in d)

Starting from the diazepinone of Preparation 9, the above mentioned compound is prepared according to the operation mode of Example 1, Process B. The melting point is 188° C.

EXAMPLE 14

5-formyl-11-(4-methylpiperazin-1-yl)-5H-pyrido(4,3-b)benzo-1,5-diazepine

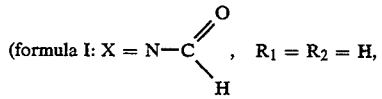

(formula I: X = N—C(=O)H, $R_1$ = $R_2$ = H, $N_1$ = pyridine with N in b', $N_2$ = benzene).

This Example starts from the compound of Example 1. 15 cc of acetic anhydride are cooled down and 7 cc of 99% formic acid are added little by little thereto under agitation. The mixture is brought for 15 minutes to 50° C. and then cooled down in an ice bath. 0.01 mole of the compound of Example 1 is added and the mixture is kept under agitation for one night. The mixture is taken up with ice, alkalinized and extracted with dichloromethane. It is dried and concentrated under vacuum and recrystallized in hexane. The melting point is 196° C.

EXAMPLE 15

11-formyl-5-(4-methylpiperazin-1-yl)-11H-pyrido(2,3-b)benzo-1,5-diazepine

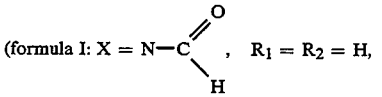

(formula I: X = N—C(=O)H, $R_1$ = $R_2$ = H, $N_1$ = pyridine with N in d', $N_2$ = benzene)

This example starts from the compound described in the article of Chakrabarti et al., J. Med. Chem., Vol. 32, No. 10, 2375–2381, 1989, which is formylated according to the process of Example 14. The melting point is 194° C.

EXAMPLE 16

11-trifluoromethylcarbonyl-5-(4-methylpiperazin-1-yl)11H-pyrido(2,3-b)benzo-1,5-diazepine (formula I: X=N—CO—CF$_3$, R$_1$=R$_2$=H, N$_1$=pyridine with N in d', N$_2$=benzene)

This example starts from the compound described in the article mentioned in Example 15. 0.02 moles of this compound are mixed with 15 ml trifluoroacetic anhydride and a few drops of N,N-dimethyl-aniline under good cooling. The resulting mixture is refluxed for 5 minutes and kept under agitation for one night. The solution is next poured onto ice, alkalinized and extracted with chloroform. The solution is then purified on a silica column and concentrated. The resulting mixture is recrystallized in hexane. The melting point is 183° C.

EXAMPLE 17

11-formyl-6-(4-methylpiperazin-1-yl)-11H-pyrido(2,3-b)benzo-1,4-diazepine

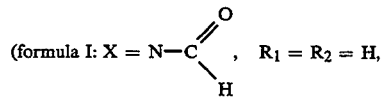

(formula I: X = N—C(=O)H, R$_1$ = R$_2$ = H,

N$_1$ = benzene, N$_2$ = pyridine with N in d)

This example starts from the compound of Example 9, which is formylated according to the operation mode of Example 14. The melting point is 202° C.

EXAMPLE 18

10-(4-methylpiperazin-1-yl)pyrido(4,3-b)benzo-1,4-thiazepine (formula I: X=S, R$_1$=R$_2$=H, N$_1$=benzene, N$_2$=pyridine with N in b)

Starting from the thiazepinone of Preparation 5, the above mentioned compound is obtained by making use of the process of Example 2. The melting point is 143°-144° C.

EXAMPLE 19

5-(4-methylpiperazin-1-yl)dibenzo(b,f)1,4-selenazepine (formula I: X=Se, R$_1$=R$_2$=H, N$_1$=N$_2$=benzene)

Starting from 10H,11H-dibenzo(b,f)1,4-selenazepine-11-one, the above mentioned compound is obtained by making use of the process of Example 2. The melting point is 107° C.

EXAMPLE 20

6-(4-methylpiperazin-1-yl)dipyrido(2,3-b: 3',2'-f)1,4-thiazepine (formula I: X=S, R$_1$=R$_2$=H, N$_1$=N$_2$=pyridine with N in d and d')

This product is prepared starting from the compound of Preparation 7 and by using the process of Example 2. The melting point is 170° C.

EXAMPLE 21

6-(4-methylpiperazin-1-yl)-11-methyl-11H-pyrido(2,3-b)benzo-1,4-diazepine (formula I: X=N—CH$_3$, R$_1$=R$_2$=H, N$_1$=benzene, N$_2$=pyridine with N in position d)

0.02 moles 2-chloro-3-nitropyridine, 0.01 mole N-methyl anthranylic acid, 5 g anhydrous K$_2$CO$_3$ and 50 ml dry isopropanol are heated with reflux for 24 hours. After evaporation of the solvent, the residue is taken up with water and is boiled in the presence of active carbon. After cooling down, the solution is acidified to a pH of about 3. The product precipitates in the form of a yellow powder and it is filtered, washed with water and dried. The melting point is 174° C.

0.005 mole of the obtained acid are suspended into anhydrous ether. The compound is esterified with diazomethane, which is prepared starting from 4 g nitrosomethylurea by decomposition of the latter in soda in the presence of ether. The ethereal solution of diazomethane is poured little by little onto the ethereal solution of the nitrated acid. Once the reaction is terminated, the solvent is evaporated. The residue is taken up with a NaHCO$_3$ solution and extracted two times with CHCl$_3$. The chloroformic solution is dried and concentrated in the presence of petrolein 100–140. The crystallized product is then filtered and washed with petrolein 40–60. The melting point is 71° C.

0.01 mole of the nitroester derivative (solubilized in 150 ml ethanol) is catalytically reduced with palladium-plated carbon (Pd/C 10%; 1 g) in a low pressure hydrogenator. After 2 hours, the reaction is terminated and the solvent is evaporated. The residue (amino-ester) is taken up with 50 ml anisole and poured into a balloon-flask. 20 ml N-methylpiperazine are added. The mixture is heated to 120° C. under agitation. A solution of 5 ml TiCl$_4$ in 10 ml anisole is poured carefully onto the mixture. The reaction medium is refluxed for 12 hours. The mixture is then cooled down and taken up with 10 ml isopropanol, 10 ml concentrated ammonia and 2 g silica. The mixture is filtered and the collected precipitate is carefully washed with chloroform. The filtrate is washed once with water and is then extracted with 2N HCl. This solution is decolored with active carbon and alkalinized with ammonia. The formed precipitate is extracted with chloroform. The chloroformic fractions are collected and concentrated into a small volume. The obtained residue is purified onto a Kiesel-gel column with a 9/1 mixture of acetone and petrolein 40–60 as eluent phase. Once isolated, the product is recrystallized in a mixture of dichloromethane and hexane. The melting point is 146° C.

The compounds of the invention have been studied in pharmacological tests for demonstrating an activity on the central or peripheral nervous system. The following results obtained for the substances of Examples 1, 10, 11, 17, 18 and 19 confirm these hypotheses and, consequently, the anti-depressant, anti-psychotic, anxiolytic, neuroleptic or sedative activity of the compounds of the invention.

| Code | In vitro: Affinity Tests onto D2 dopaminergic and muscarinergic receptors | |
|---|---|---|
| | Inhibition, % (binding of $^3$H-spiperone) | Inhibition, % (binding of $^3$H QNB) |
| Clozapine | 57.3 | 80.35 |
| Clothiapine | 94.6 | 38.05 |
| Haloperidol | 100 | 0 |
| Example 1 | 56.2 | 4.48 |
| Example 10 | 31.5 | 62.08 |
| Example 11 | 24.8 | 67.3 |
| Example 17 | 22.8 | 43.38 |
| Example 18 | 50.2 | 57.61 |
| Example 19 | 26.7 | 78.31 |

D2 Dopaminergic Receptors

Characterization by ($^3$H) spiperone displacement test.

Preparation of the Membranes

The brain of male Wistar rats (200–250 g) is removed. The striatum is dissected rapidly and homogenized into 20 ml iced buffer (50 nM Tris/HCl, pH=7.4, 25° C.) by means of a Teflon homogenizer. The homogenate is centrifuged at 4° C. at 10000 G during 10 minutes, the concentrate is washed two times with iced buffer and recentrifuged. The final concentrate is suspended into iced buffer (50 nM/HCl, pH=7.4) containing 5 nM magnesium sulfate, 0.5 nM EDTA. After rehomogenization, the suspension is adjusted to 1 mg proteine per ml. Le protein quantity is determined by the method of Lowry et al. [J. Biol. Chem. 193, 265-275 (1951)] wherein bovine serumalbumine is used as standard.

Binding Test

A method inspired by Tecott et al. [Biol. Psychiatry 21, 1114-1122 (1986)] is used. The binding of ($^3$H)-spiperone is evaluated onto the following mixture: 200 μl membrane preparation (0.1–0.2 mg proteine), 100 μl ($10^{-6}$M) test substance and 600 μl buffer for a final volume of 1 ml. Control tubes, which are taken as a reference of the nonspecific binding, contain also 1 μM (+) butaclamol. The samples (in threefold) are then incubated with 0.5 nM ($^3$H)spiperone at 25° C. for 60 minutes. This step is stopped by a quick vacuum filtration of the suspension through a glass-fiber filter GF/C. The filter is rinsed three times with 5 ml iced buffer. The radioactivity is measured with a liquid scintillation spectrometer (LKB Rack Beta 1219). The results are given by the difference of percentage between the control (1 μM (+)butaclamol) and the tested substance.

CHARACTERIZATION OF THE MUSCARINIC RECEPTORS

Bindings to the Receptors

The method is inspired by the technique described by Yamamura and Snyder [Proc. Natl. Sci. USA 71, 1725 (1974)]. After a rapid removal, the CFY rat brain (130–180 g) is dissected to eliminate the cerebellum. The other tissues are homogenized with a "Potter" in a solution of 0.32M saccharose and the 50 mM Tris/HCl buffer of pH 7.5. The protein concentration is determined according to the Peterson method [Anal. Biochem. 83, 346 (1977)].

The binding test is performed in threefold at 25° C. The incubation medium (1 ml) is composed of 60 mM NaCl, Tris/HCl buffer of pH 7.5 and 1.5 nM ($^3$H) QNB (New England Nuclear, specific act.: 1.18 TBq/mole). The reaction is maintained for 60 minutes with a homogenate containing 250–400 μg protein. The non-specific binding is realized by $10^{-5}$M atropin. The treatment is stopped by a quick filtration onto a Whatman glass filter GF/C. The free ligand is eliminated in this way. Each sample is washed with 2×10 ml cold buffer. The filters are dried, put into a toluenic solution for scintillation and placed in a scintillation counter (Packard Tricarb liquid scintillation counter) during one day. The receptor binding is directly proportional to the protein concentration upto 700 μg protein per ml.

In vivo: Apomorphine Antagonism Test

At 20 mg/kg, most of the compounds reduce the locomotion by the animals and possess a sedative effect. In most of the cases, the compounds present an activity, the intensity of which is comprised between the one of clozapine (20 mg/g) (+) and the one of haloperidol (0.63 mg/kg) (+++++). The following results are provided by way of example.

| | |
|---|---|
| Example 1 | ++ |
| Example 5 | + |
| Example 7 | + |
| Example 8 | +++ |
| Example 10 | +++ |
| Example 11 | +++ |
| Example 12 | + |
| Example 13 | + |
| Example 19 | ++ |

Catalepsy Test

See in particular GRAY W. D., OSTERBERG A. C., RAUH C. E., Arch. Int. Pharmacodyn. 134, 198, 1961 and COSTALL B., OLLEY J. E., Neuropharmacology 10, 297, 1971.

This test is representative for the extrapyramidal effects present in numerous neuroleptics (unwanted secondary effect). The compounds of the invention cause very little catalepsy and seem therefore to be free from this unwanted secondary effect. However, some products have shown a slight catalepsy:

Examples 1 and 3: catalepsy for doses above 40 mg/kg

Example 4: slight cataleptic effect starting from 20 mg/kg

Clozapine: week cataleptic effect starting from 20 mg/kg.

The present invention relates also to pharmaceutical compositions which contain as active constituants one or more compounds of formula (I), either alone or with other active substances having similar or different effects, in a mixture with an appropriate pharmaceutical excipient.

These pharmaceutical compositions can be solids such as one or more layered uncovered or coated tablets, cachets, capsules, dispersable or soluble powders, suppositories, or liquids such as solutions, collyria, suspensions, emulsions, syrups, preparations destined for parenteral administration, for example in the form of an aerosol.

The solid compositions for oral use can be prepared by mixing one or more substances in accordance with the invention for example with milk sugar, powder sugar, starch, talc, with products destined to delay or to prolong the effects, for example cellulose acetophthalate, glyceryl stearates, ion exchanging resins.

The suppositories can be prepared by incorporating one or more substances in accordance with the invention for example into cacao butter or into any other appropriate substance, such as the mono-, di- and triglycerides of saturated fatty acids.

The liquid compositions can be prepared for example by dissolving, suspending or emulsifying, at the time of preparation or directly before the administration, one or more substances in accordance with the invention and moreover any other product, the presence of which is considered to be desired or necessary, such as for example preserving agents such as methyl and propyl p-hydroxybenzoates, thickeners and emulsifiers such as cellulose derivatives and sorbitane polyoxyethylene esters, sweeteners and aromatic substances such as sugar, saccharin, sorbitol, natural or synthetic spirits, isotonizisers as sodium chloride, or buffers such as sodium phosphates in distilled water, in other acceptable hydroxylated liquids such as ethanol, glycerin, certain glycols, in mixtures of these solvents or in pharmaceutically acceptable oils.

What is claimed is:

1. A methylpiperazinoazepine compound corresponding to formula (I) or a pharmaceutically acceptable salt thereof:

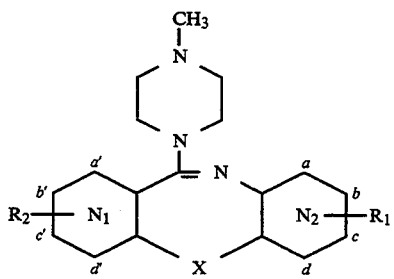

wherein:

X represents an oxygen atom, a sulfur atom, a selenium atom or NH- or $NR_3$-group wherein $R_3$ represents a

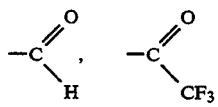

group or a straight or branched alkyl group of 1 to 4 carbon atoms;

$R_1$ represents a hydrogen atom, a halogen atom or a straight or branched alkyl group of 1 to 4 carbon atoms;

$R_2$ represents a hydrogen atom, a halogen atom or a straight or branched alkyl group of 1 to 4 carbon atoms; and $N_1$ represents a benzene ring and $N_2$ a pyridine ring or vice versa, wherein the nitrogen atom of the pyridine ring is in the b, b', d or d' position, and with the proviso that, when $R_1$ and $R_2$ represent hydrogen and X represents sulfur, oxygen or an NH-group, $N_1$ is pyridine and $N_2$ is benzene and the pyridine nitrogen is excluded from position d', both $N_1$ and $N_2$ can be benzene when X represents a selenium atom, and both $N_1$ and $N_2$ can be pyridine when X represents a sulfur atom.

2. The compound as claimed in claim 1, wherein $R_1$ represents a hydrogen atom, a chlorine atom, a fluorine atom or a methyl group.

3. The compound as claimed in claim 1, wherein $R_2$ represents a hydrogen atom or a chlorine atom.

4. The compound as claimed in claim 1, which is formed by a salt selected from the group comprising hydrochlorides, hydrobromides, sulfates, phosphates, acetates, citrates, maleates, fumarates and methanesulfonates.

5. The compound as claimed in claim 1, which is selected from the group comprising:
11-(4-methylpiperazin-1-yl)-5H-pyrido(4,3-b)benzo-1,5-diazepine;
8-chloro-6-(4-methylpiperazin-1-yl)pyrido(2,3-b)benzo-1,4-thiazepine fumarate;
5-(4-methylpiperazin-1-yl)pyrido(2,3-b)benzo-1,5-oxazepine maleate;
8-chloro-5-(4-methylpiperazin-1-yl)pyrido(2,3-b)benzo-1,5-oxazepine fumarate;
5-(4-methylpiperazin-1-yl)-8-methylpyrido(2,3-b)benzo-1,5-oxazepine fumarate;
8-chloro-6-(4-methylpiperazin-1-yl)pyrido(2,3-b)benzo-1,4-oxazepine fumarate;
8-chloro-6-(4-methylpiperazin-1-yl)-11H-pyrido(2,3-b)benzo-1,4-diazepine;
6-(4-methylpiperazin-1-yl)-8-methyl-11H-pyrido(2,3-b)benzo-1,4-diazepine;
9-chloro-6-(4-methylpiperazin-1-yl)-11H-pyrido(2,3-b)benzo-1,4-diazepine;
8-fluoro-6-(4-methylpiperazin-1-yl)-11H-pyrido(2,3-b)benzo-1,4-diazepine;
5-formyl-11-(4-methylpiperazin-1-yl)-5H-pyrido(4,3-b)benzo-1,5-diazepine;
11-formyl-5-(4-methylpiperazin-1-yl)-11H-pyrido(2,3-b)benzo-1,5-diazepine;
11-trifluoromethylcarbonyl-5-(4-methylpiperazin-1-yl)-11H-pyrido(2,3-b)benzo-1,5-diazepine;
11-formyl-6-(4-methylpiperazin-1-yl)-11H-pyrido(2,3-b)benzo-1,4-diazepine;
5-(4-methylpiperazin-1-yl)dibenzo(b,f)1,4-selenazepine;
6-(4-methylpiperazin-1-yl) dipyrido(2,3-b:3',2'-f)1,4-thiazepine.

6. A process for preparing a methylpiperazinoazepine compound corresponding to formula (I) of claim 1, wherein X is NH or N—$R_3$, and $R_1$, $R_2$, $R_3$, $N_1$ and $N_2$ are defined as in claim 1, in which process the compound of formula (I) is prepared starting from a compound corresponding to formula (II):

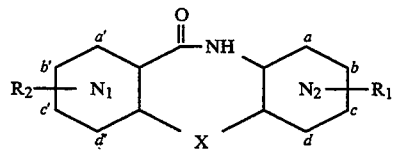

wherein X is NH or N—$R_3$, and $R_1$, $R_2$, $R_3$ are such as defined as in claim 1 and wherein $N_1$ and $N_2$ each represent a benzene ring or a pyridine ring, said process comprising the steps of:

(a) reacting said compound of formula (II) with $P_2S_5$ to form a thione compound of the following formula (III):

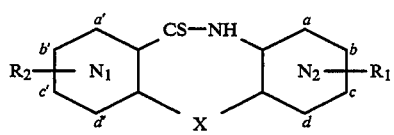

(b) reacting said thione compound of formula (III) with paranitrobenzyl chloride in the presence of tert-butylate of potassium to form a thioether of the following formula (IV):

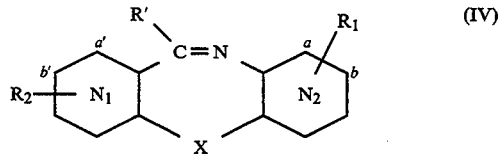

wherein $R_1$ is paranitrobenzyl (c) reacting said thioether of formula (IV) with N-methylpiperazine to form a methylpiperazinoazepine compound of formula (I).

7. A process for preparing a methylpiperazinoazepine compound corresponding to formula (I) of claim 1, wherein X, R₁, R₂, N₁ and N₂ are defined as in claim 1, in which process the compound of formula (I) is prepared starting from the reaction product of an orthohalogeno nitropyridine of formula (V):

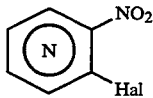

wherein Hal represents a halogen atom, and a benzenecarboxylic acid of formula (VI):

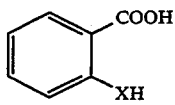

wherein X is defined as in claim 1, said process comprising esterifying the reaction product of the compound of formula (V) and the compound of formula (VI), to form a nitroester, reducing the nitroester to obtain an aminoester and reacting the amino-ester with N-methylpiperazine to obtain the compound of formula (I).

8. A pharmaceutical composition comprising an effective amount of a compound as claimed in claim 1 and a pharmaceutically acceptable excipient.

9. A process for preparing a methylpiperazinoazepine compound corresponding to formula (I) of claim 1, wherein X is NH or N—R₃, R₁, R₂, R₃, N₁ and N₂ are defined as in claim 1, in which process the compound of formula (I) is prepared starting from a compound corresponding to the following formula (II):

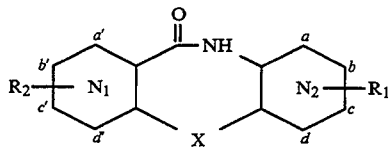

wherein X is NH or N—R₃, and R₁, R₂, and R₃ are such as defined as in claim 1, and wherein N₁ and N₂ each represent a benzene ring or a pyridine ring, said process comprising mixing and reacting said compound of formula (II) with methylpiperazine to form a methylpiperazinoazepine compound of formula (I).

10. A process for preparing a methylpiperazinoazepine compound corresponding to formula (I) of claim 1, where X is selected from the group consisting of oxygen, selenium and sulfur, and R₁, R₂, N₁ and N₂ are defined as in claim 1, in which the compound of formula (I) is prepared starting from the following compound of formula (II):

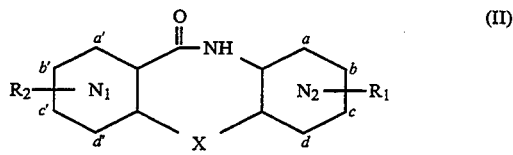

wherein X is selected from the group consisting of oxygen, selenium and sulfur, and R₁ and R₂ are such as defined in claim 1 and where N₁ and N₂ each represent a benzene ring or a pyridine ring, said process comprising the steps of:

(a) reacting said compound of formula (II) with phosphorus oxychloride to form an iminochloride of the following formula (V):

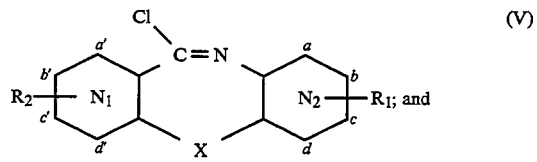

(b) reacting said compound of formula (V) with N-methylpiperazine to form a compound according to said formula (I).

11. A method for affecting an activity of a central or peripheral nervous system, comprising administering a pharmaceutically effective amount of the compound of claim 1.

12. The method of claim 11, wherein the activity is selected from the group consisting of antidepressive, antipsychotic, anxiolytic, neuroleptic and sedative activities.

13. 6-(4-methylpiperazin-1-yl)pyrido(2,3-b)benzo-1,4-thiazepine.

14. 6-(4-methylpiperazin-1-yl)pyrido(2,3-b)benzo-1,4-oxazepine fumarate.

15. 6-(4-methylpiperazin-1-yl)-11H-pyrido(2,3-b)benzo-1,4-diazepine.

16. 10-(4-methylpiperazin-1-yl)pyrido(4,3-b)benzo-1,4-thiazepine.

17. 6-(4-methylpiperazin-1-yl)dipyrido(2,3-b: 3',2'-f)1,4-thiazepine.

* * * * *